United States Patent
Tian et al.

(10) Patent No.: US 11,454,681 B1
(45) Date of Patent: Sep. 27, 2022

(54) MAGNETIC PARTICLE IMAGING METHOD BASED ON NON-IDEAL FIELD FREE POINT

(71) Applicant: Beijing University of Aeronautics and Astronautics, Beijing (CN)

(72) Inventors: Jie Tian, Beijing (CN); Yimeng Li, Beijing (CN); Yu An, Beijing (CN); Jing Zhong, Beijing (CN); Haoran Zhang, Beijing (CN); Yanjun Liu, Beijing (CN)

(73) Assignee: Beijing University of Aeronautics and Astronautics

( * ) Notice: Subject to any disclaimer, the term of this patent is extended or adjusted under 35 U.S.C. 154(b) by 0 days.

(21) Appl. No.: 17/833,275

(22) Filed: Jun. 6, 2022

(51) Int. Cl.
  *G01R 33/12* (2006.01)

(52) U.S. Cl.
  CPC .................. *G01R 33/1276* (2013.01)

(58) Field of Classification Search
  CPC .................................. G01R 33/1276
  See application file for complete search history.

(56) References Cited

FOREIGN PATENT DOCUMENTS

| WO | WO-2011116229 A2 * | 9/2011 | ............... A61B 5/05 |
| WO | WO-2011121487 A1 * | 10/2011 | ............... A61B 5/05 |

OTHER PUBLICATIONS

Goodwill PW, Konkle JJ, Zheng B, Saritas EU, Conolly SM. Projection x-space magnetic particle imaging. IEEE Trans Med Imaging. May 2012;31(5) (Year: 2012).*

Thomas März et al., Model-Based Reconstruction for Magnetic Particle Imaging in 2D and 3D, arXiv:1605.08095 [math.NA], 2016 (Year: 2016).*

* cited by examiner

*Primary Examiner* — Daniel R Miller (57) ABSTRACT

A magnetic particle imaging method based on a non-ideal Field Free Point (FFP), including the following steps: setting external magnetic field conditions of a non-ideal FFP and an ideal FFP, and obtaining a magnetization vector M of Superparamagnetic Iron Oxide Nanoparticles (SPIOs) and a Point Spread Function (PSF) in combination with a Langevin function; obtaining a signal feature on basis of a voltage signal of a detection coil of a Magnetic Particle Imaging (MPI) instrument; performing integral transformation on the voltage signal collected by the detection coil of the MPI instrument to obtain a voltage signal of an equivalent ideal FFP; averaging the moving speed of an FFP of the MPI instrument to obtain a moving speed of the equivalent ideal FFP; obtaining an equivalent Three-Dimensional concentration reconstruction image on basis of the voltage signal of the equivalent ideal FFP and a moving speed of the equivalent ideal FFP.

8 Claims, 9 Drawing Sheets

MAGNETIC PARTICLE IMAGING METHOD BASED ON NON-IDEAL FIELD FREE POINT

TECHNICAL FIELD

The present invention relates to the field of magnetic particle imaging, and particularly relates to a magnetic particle imaging method based on a non-ideal Field Free Point (FFP).

BACKGROUND

Magnetic Particle Imaging (MPI) is a novel imaging method. Under MPI, an FFP area is constructed by combining a high-gradient selection field and a low-frequency focusing field. Superparamagnetic Iron Oxide Nanoparticles (SPIOs) in the FFP area generate a response to an excitation magnetic field, while the SPIOs in other areas are in a magnetic saturation state under a combined action of the selection field and the focusing field and do not have a response to the excitation magnetic field. Therefore, a voltage signal collected by a detection coil only includes a magnetic particle response in the FFP area and does not include a magnetic particle response in other areas, so that performing spatial coding reconstruction on magnetic particle distribution information can be conducted, and accurate positioning of a detection object can be accomplished.

The existing image reconstruction methods of MPI are all based on the assumption that "the position of an instantaneous FFP is unique in space", and that the value of a pixel point in a reconstructed image is jointly determined by induced voltages of a plurality of FFPs in a corresponding view field. Under ideal conditions, the magnetic fields at all positions are zero in each FFP area, and the SPIOs generate a magnetization vector only under the action of an Alternating Current (AC) driving magnetic field. In an actual MPI device, it is not possible that all positions are absolutely field-free in the same FFP area. Especially, in a process of manufacturing an MPI instrument with a large view field, an ideal FFP cannot be guaranteed.

The SPIOs at a non-ideal FFP are not only affected by the AC driving magnetic field, but also by a low-amplitude Direct Current (DC) magnetic field applied by the selection field and the focusing field, resulting in the asymmetric excitation of the SPIOs, the difference between the magnetization vector and the magnetization vector under the ideal condition, and the change of an induced voltage of the detection coil. It is precisely because there is a non-ideal FFP in the actual MPI device, errors and artifacts will be inevitably produced by using the existing MPI-based image reconstruction methods under the ideal condition.

SUMMARY

In view of the deficiencies in the prior art, the present disclosure provides a magnetic particle imaging method based on a non-ideal FFP. By this method, a magnetic field response model of a non-ideal FFP is constructed, and the difference between a voltage signal of an ideal FFP and a voltage signal of the non-ideal FFP is analyzed on the basis of the model, so that an image reconstruction algorithm for the non-ideal FFP is provided, and a high-quality image reconstruction result is obtained.

The technical solution of the present disclosure is as follows:

A magnetic particle imaging method based on a non-ideal FFP includes the following steps:

S1, setting external magnetic field conditions of a non-ideal FFP and an ideal FFP, and obtaining a magnetization vector M of SPIOs and a Point Spread Function (PSF) in combination with a Langevin function;

S2, obtaining a signal feature on the basis of a voltage signal of a detection coil of an MPI instrument with non-ideal FFP and ideal FFP magnetic field distribution;

S3, performing integral transformation on the voltage signal collected by the detection coil of the MPI instrument on the basis of the signal feature obtained in S2, so as to obtain a voltage signal of an equivalent ideal FFP;

S4, averaging the moving speed of an FFP of the MPI instrument on the basis of the obtained signal feature, so as to obtain a moving speed of the equivalent ideal FFP;

S5, obtaining an equivalent Three-Dimensional (3D) reconstruction image on the basis of the voltage signal of the equivalent ideal FFP obtained in S3 and the moving speed of the equivalent ideal FFP obtained in S4.

Further, the external magnetic field conditions of the non-ideal FFP and the ideal FFP in S1 are as follows:

The DC magnetic field intensity of all positions of in the ideal FFP area is G'=0, and the external AC driving magnetic field intensity $H_D$ is not affected: $H_D=A \cos(2\pi f_D t)$.

Only the magnetic field intensity in a central area of the non-ideal FFP is H=0; there is a static magnetic field with the DC magnetic field intensity of G in a peripheral area; the magnetic field intensity on one side of the central area is G>0, and the magnetic field intensity on one side of the central area is G<0; the combined excitation field produced by the static magnetic field and the external AD driving magnetic field is:

$$H_{SPIO}=H_D+G=A \cos(2\pi f_D t)+G$$

Where, $H_D$ is the external AD driving magnetic field, A is an amplitude of the AD driving magnetic field, $f_D$ is the frequency of the AD driving magnetic field, and t is time.

Further, S1 further includes: generating the magnetization vector M by the SPIOs according to the Langevin function under the action of the external magnetic field, so as to obtain the PSF of the SPIOs at the non-ideal FFP and the ideal FFP:

$$PSF = \frac{dM}{dt}.$$

Further, S2 further includes:

the DC magnetic field intensity of each position at the ideal FFP is G'=0, and the voltage signal of the detection coil of the MPI instrument is the sum of the PSFs at all positions S:

$$U_{ideal} = \sum_S PSF_{G'=0}$$

The DC magnetic field intensity of part positions $S_1$ of the non-ideal FFP is G>0, the DC magnetic field intensity of part positions $S_2$ is G=0, the DC magnetic field intensity of remaining positions $S_3$ is G<0, and the voltage signal of the detection coil is the sum of the PSFs of the three parts of positions:

$$U_{real} = \sum_{S_1} PSF_{G>0} + \sum_{S_2} PSF_{G=0} + \sum_{S_3} PSF_{G<0}.$$

The voltage signal of the ideal FFP is compared with the voltage signal of the non-ideal FFP, to obtain a common signal feature of the two.

Further, the common signal feature is: in the same half cycle, the integrals of voltage amplitudes along time are approximately equal:

$$\int_t U_{ideal} \approx \int_t U_{real}$$

Further, S3 further includes:
performing integration on the voltage signal every half cycle along time to obtain a voltage signal of an equivalent ideal FFP, which is as follows:

$$\tilde{u}(n) = \int_n^{n+\frac{T_D}{2}} u(t)dt$$

Where, u(t) is the voltage signal collected by the detection coil of the MPI instrument, the $T_D$ is a cycle, $$\frac{1}{2}T_D = \frac{1}{2f_D},$$

and n=0, 1, 2 . . . .
Further, S4 further includes:
averaging the moving speed of the FFP in every half cycle, so as to obtain the moving speed of the equivalent ideal FFP:

$$\tilde{\dot{x}}_s(n) = \frac{\int_n^{n+\frac{T_D}{2}} \dot{x}_s(t)dt}{\frac{T_D}{2}}$$

Where, $\dot{x}_s(t)$ is the moving speed of the FFP caused by the focusing field in MPI, n=0, 1, 2 . . . .
Further, S5 further includes:
dividing the voltage signal of the equivalent ideal FFP by the moving speed of the equivalent ideal FFP to obtain an image value at a corresponding position, which is as follows:

$$IMG_n = \tilde{u}(n)/\tilde{\dot{x}}_s(n);$$

splicing the image values at various positions according to a moving track of the FFP, so as to obtain an equivalent 3D concentration reconstruction image.

Compared with the prior art, the present disclosure has the following beneficial effects:

The magnetic particle imaging method based on the non-ideal FFP of the present disclosure is provided on the basis of a magnetic field condition of the non-ideal FFP. The response of the SPIOs in a non-ideal FFP area and the voltage signal feature of the detection coil are analyzed, and the image values are solved by obtaining the voltage signal of the equivalent ideal FFP and the moving speed of the equivalent FFP, so as to obtain a reconstructed image. By the method, the artifacts and phase errors of image reconstruction caused by the fact that the FFP in the actual MPI instrument is not an ideal Field Free Area are reduced, the deficiencies of the traditional reconstruction method that ignores an actual non-ideal FFP condition are overcome, and the reconstruction quality and the resolution are greatly improved.

In addition, the imaging method of the present disclosure has the universality for different structure types of FFP-MPI devices and different tracers, can overcome the deficiencies that the current MPI hardware structure cannot achieve high-precision uniform FFPs, improves the image quality from the perspective of a reconstruction algorithm, and also provides the possibility for the realization of large view-field MPI.

BRIEF DESCRIPTION OF THE DRAWINGS

The present disclosure can be better understood by referring to the accompanying drawings. The components in the drawings should not be regarded as drawn to scale, and the emphasis should be placed upon illustrating the principle of the present disclosure.

DETAILED DESCRIPTION OF THE EMBODIMENTS

In order to facilitate the understanding and implementation of the present disclosure by those skilled in the art, the present disclosure will be further described in detail below with reference to the accompanying drawings and specific implementation modes.

Figure 1:
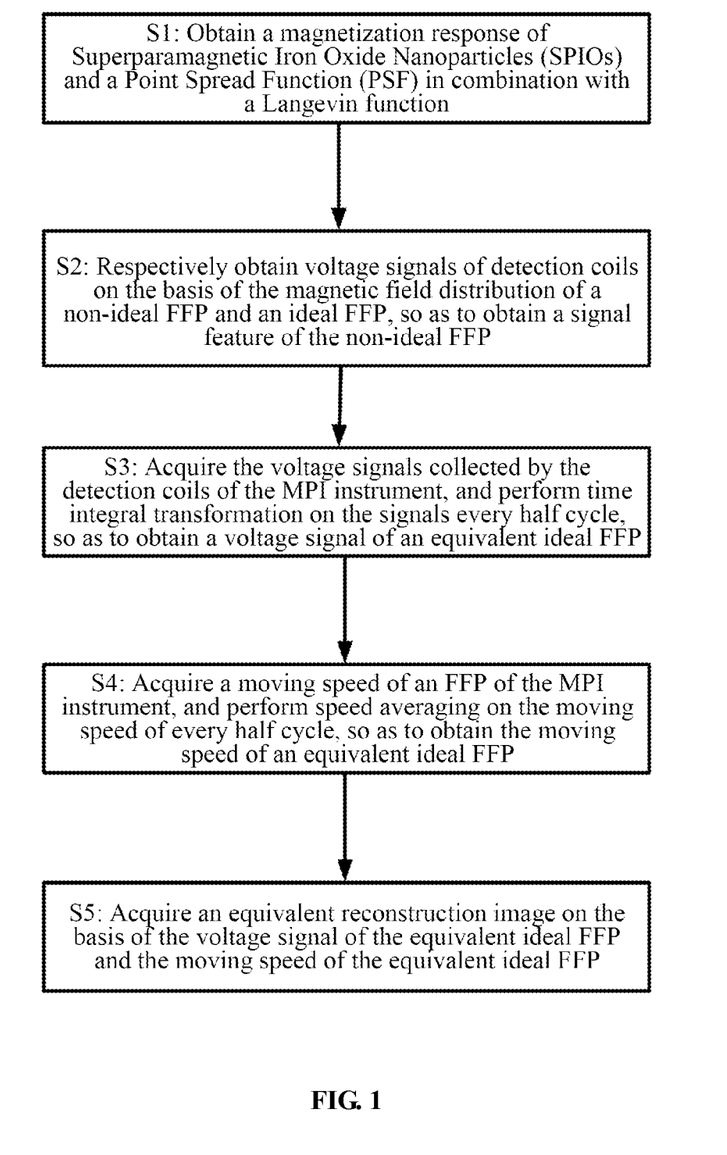
FIG. 1 illustrates a flowchart of a magnetic particle imaging method based on a non-ideal FFP of the present disclosure.
Figure 2:
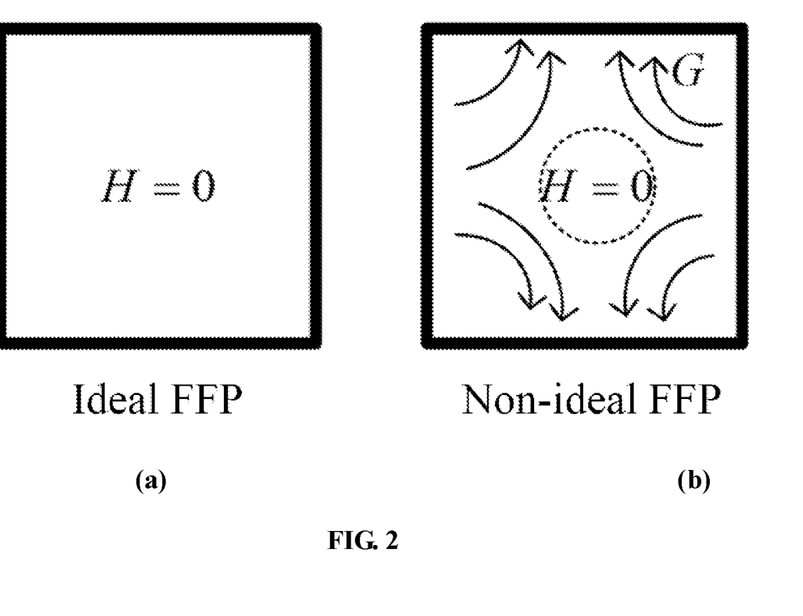
FIG. 2 illustrates a schematic diagram of magnetic field conditions of an ideal FFP and the non-ideal FFP.

A technical solution of a magnetic particle imaging method based on a non-ideal FFP provided by the present disclosure is as shown in FIG. 1. A specific implementation solution thereof is as follows:

S1, external magnetic field conditions of a non-ideal FFP and an ideal FFP are set, and a magnetization vector M of SPIOs and a PSF are obtained in combination with a Langevin function:

the ideal FFP and the non-ideal FFP are as shown in FIG. 2, where the DC magnetic field intensity of all positions of in the ideal FFP area is G'=0, an alternating current is introduced into a driving coil, and the generated external AC driving magnetic field intensity $H_D$ is not affected: $H_D = A \cos(2\pi f_D t)$. However, it is not the case in actual MPI, but a non-ideal FFP. Only the magnetic field intensity in a central area of the non-ideal FFP is H=0; there is a static magnetic field with the DC magnetic field intensity of G in a peripheral area; the magnetic field intensity on one side of the central area is G>0, and the magnetic field intensity on one side of the central area is G<0; in a peripheral area of the non-ideal FFP, the existence of the static magnetic field adds a DC component to the external AC driving magnetic field, and the produced combined excitation field is:

$$H_{SPIO} = H_D + G = A \cos(2\pi f_D t) + G.$$

Where, $H_D$ is the external AD driving magnetic field, A is an amplitude of the AD driving magnetic field, $f_D$ is the frequency of the AD driving magnetic field, and t is time.

Figure 3:
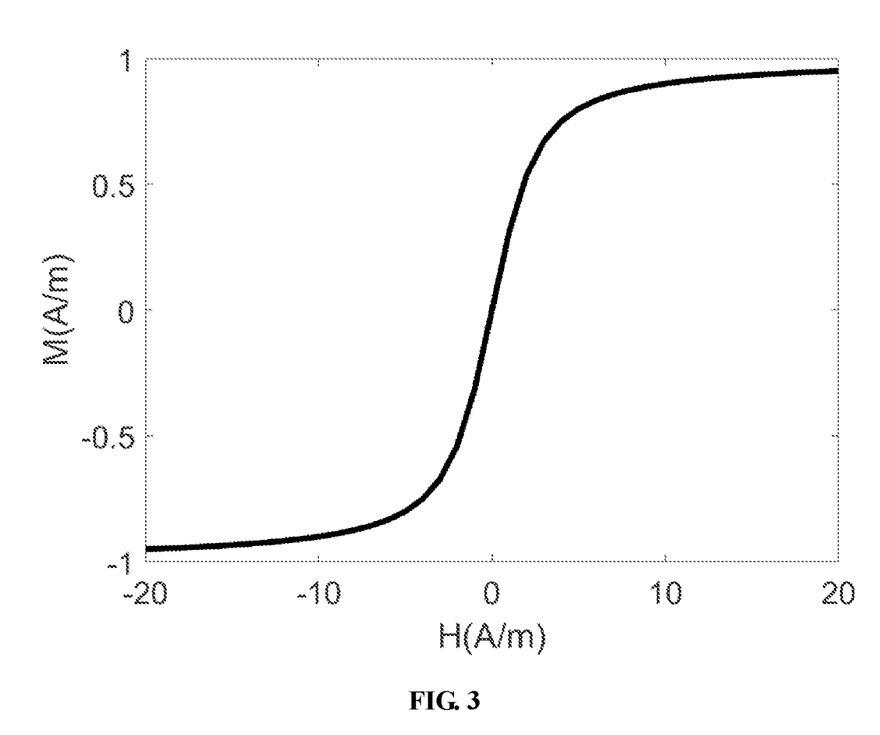
FIG. 3 illustrates a Langevin function curve.
Figure 4:
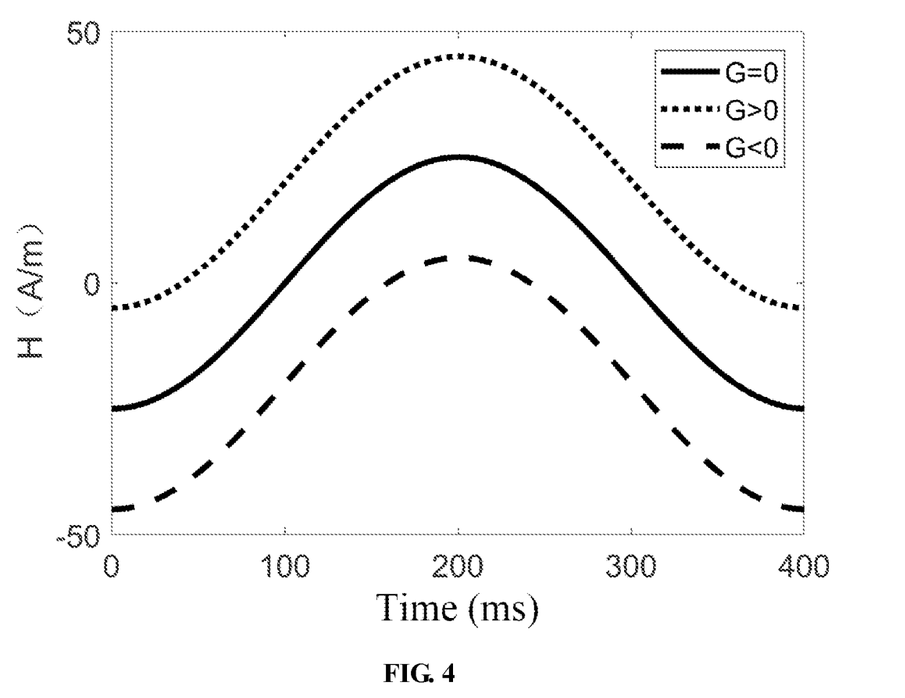
FIG. 4 illustrates a combined excitation field of the ideal FFP and the non-ideal FFP.
Figure 5:
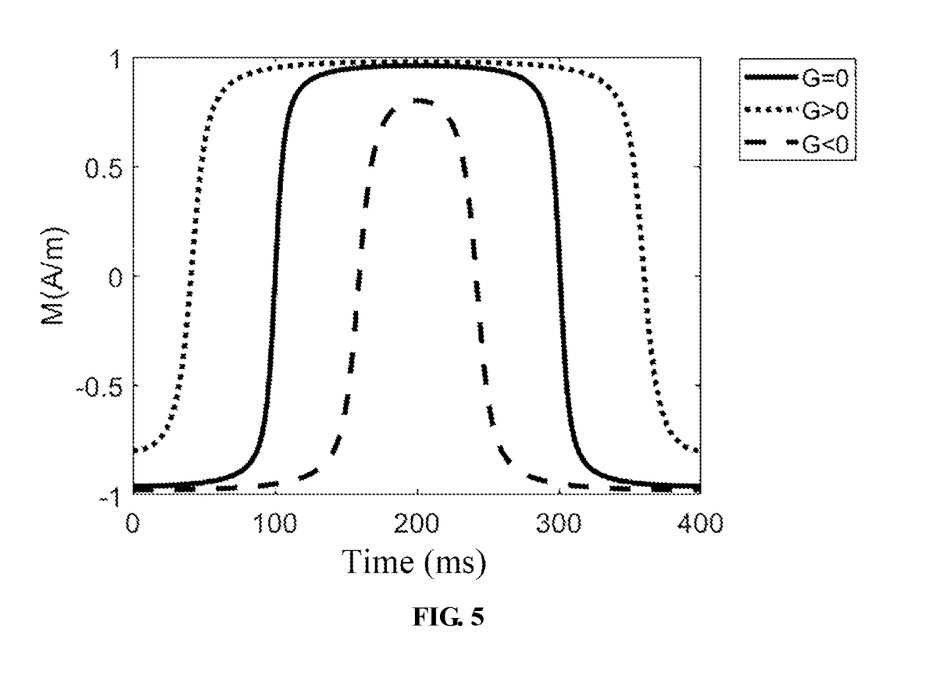
FIG. 5 illustrates a magnetization vector of the ideal FFP and the non-ideal FFP.
Figure 6:
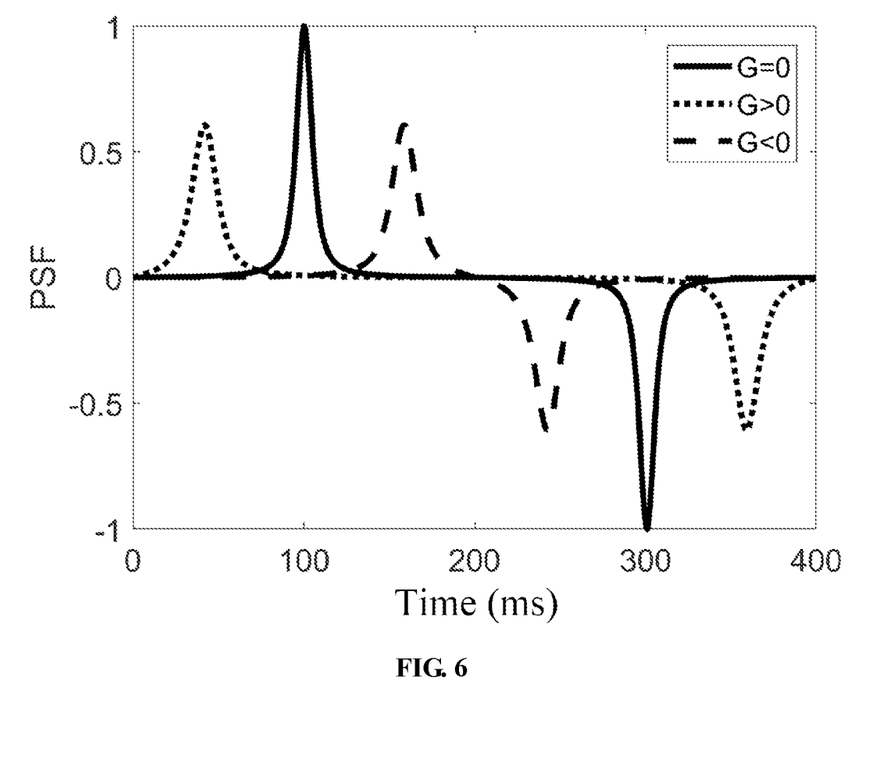
FIG. 6 illustrates PSFs of the ideal FFP and the non-ideal FFP.

As shown in FIGS. 3 to 5, the magnetization vector M is generated by the SPIOs according to the Langevin function under the action of the external magnetic field, and the PSFs of the SPIOs at the non-ideal FFP and the ideal FFP are obtained on the basis of the change rate dM/dt of the magnetization vector M along time, as shown in FIG. 6:

$$PSF = \frac{dM}{dt}.$$

S2, a signal feature is obtained on the basis of a voltage signal of a detection coil of an MPI instrument with non-ideal FFP and ideal FFP magnetic field distribution:

the DC magnetic field intensity of each position at the ideal FFP is G'=0, and the voltage signal of the detection coil of the MPI instrument is the sum of the PSFs at all positions S:

$$U_{ideal} = \sum_{S} PSF_{G'=0}$$

the DC magnetic field intensity of part positions S1 of the non-ideal FFP is G>0, the DC magnetic field intensity of part positions S2 is G=0, the DC magnetic field intensity of remaining positions S3 is G<0, and the voltage signal of the detection coil is the sum of the PSFs of the three parts of positions:

$$U_{real} = \sum_{S_1} PSF_{G>0} + \sum_{S_2} PSF_{G=0} + \sum_{S_3} PSF_{G<0}$$

Figure 7:
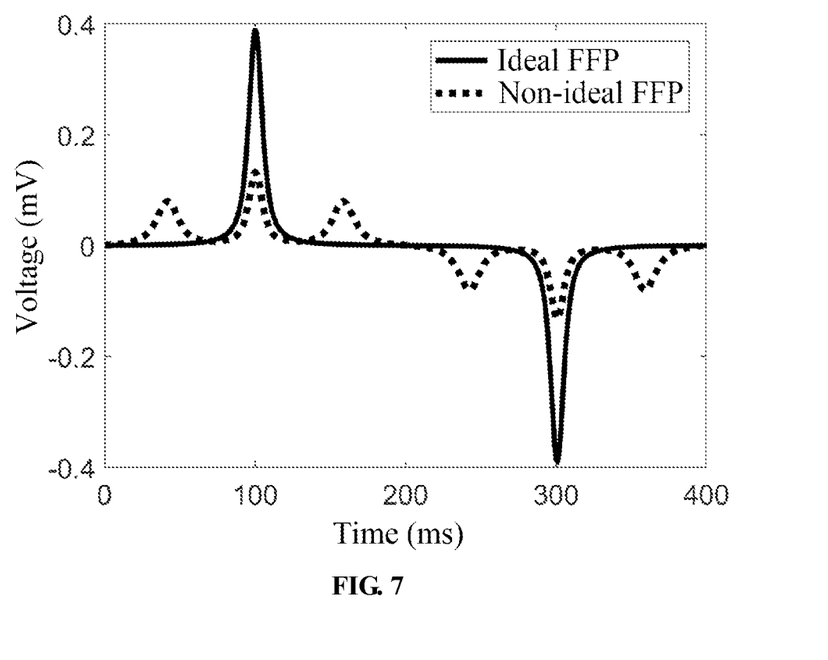
FIG. 7 illustrates voltage signals of the ideal FFP and the non-ideal FFP.

The voltage signal of the ideal FFP and the voltage signal of the non-ideal FFP are as shown in FIG. 7, the common feature of the two is that: in the same half cycle, the integrals of voltage amplitudes along time are approximately equal:

$$\int_t U_{ideal} \approx \int_t U_{real}.$$

S3, time integral transformation is performed on the voltage signal collected by the detection coil of the MPI instrument, so as to obtain a voltage signal of an equivalent ideal FFP:

Integration is performed on the voltage signal every half cycle along time to obtain a voltage signal of an equivalent ideal FFP, which is as follows:

The voltage signal collected by the detection coil of the MPI instrument is u(t), and the half cycle of the excitation coil is:

$$\frac{1}{2}T_D = \frac{1}{2f_D}$$

Integration is performed on the u(t) of every $\frac{1}{2}T_D$ along time to obtain the voltage signal of the equivalent ideal FFP, which is as follows:

$$\tilde{u}(n) = \int_{n}^{n+\frac{T_0}{2}} u(t)dt$$

Where, n=0, 1, 2 . . . .

S4, the moving speed of the FFP of the MPI instrument is averaged very half cycle, so as to obtain a moving speed of the equivalent ideal FFP;

the moving speed of the FFP is averaged in every half cycle, so as to obtain the moving speed of the equivalent ideal FFP:

$$\tilde{\dot{x}}_s(n) = \frac{\int_{n}^{n+\frac{T_0}{2}} \dot{x}_s(t)dt}{\frac{T_D}{2}}$$

Where, $\dot{x}_s(t)$ is the moving speed of the FFP caused by the focusing field in MPI, and n=0, 1, 2 . . . .

S5, an equivalent 3D concentration reconstruction image is obtained on the basis of the voltage signal of the equivalent ideal FFP and the moving speed of the equivalent ideal FFP:

the voltage signal of the equivalent ideal FFP is divided by the moving speed of the equivalent ideal FFP to obtain an image value at a corresponding position, which is as follows:

$$IMG_n = \tilde{u}(n)/\tilde{\dot{x}}_s(n).$$

The image values at various positions are spliced according to a moving track of the FFP, so as to obtain an equivalent 3D concentration reconstruction image.

Figure 8:
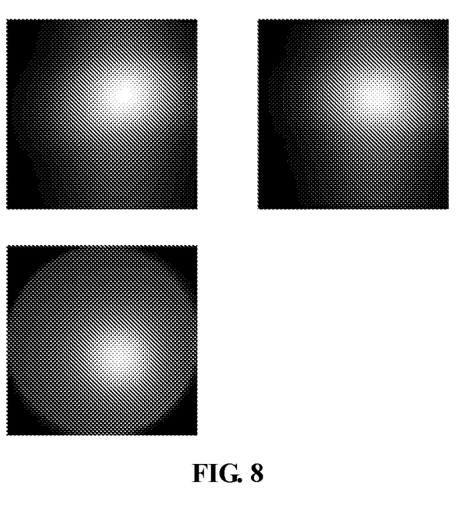
FIG. 8 illustrates three views of two ellipsoid samples with different concentrations reconstructed on the basis of the ideal FFP.
Figure 9:
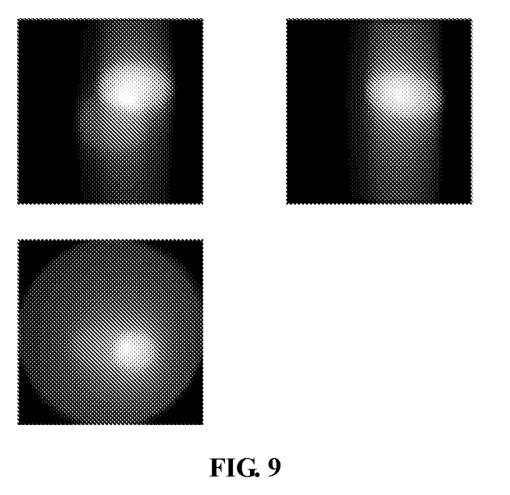
FIG. 9 illustrates three views of two ellipsoid samples with different concentrations reconstructed by the method of the present disclosure on the basis of the non-ideal FFP.

FIG. 8 illustrates three views of two ellipsoid samples with different concentrations reconstructed ignoring the actual condition that the FFP is under a non-ideal condition. The image result is only a cloud of light, which cannot clearly distinguish the two ellipsoid samples. FIG. 9 illustrates three views of two ellipsoid samples with different concentrations reconstructed by the method of the present disclosure, and the two ellipsoids can be distinguished clearly. By comparing FIG. 8 and FIG. 9, it can be seen that the method of the present disclosure considers a condition of non-ideal FFP, and the influence of the non-ideal FFP is fused into an image reconstruction process, the artifacts of the obtained image are reduced, the image quality is obviously improved, and the resolution is greatly improved.

In the present disclosure, unless otherwise definitely specified and limited, terms "mount", "mutually connect", "connect", "fix", etc. should be broadly understood. For example, the terms may refer to fixed connection, or may also refer to detachable connection or integration. The terms may refer to mechanical connection and may also refer to electrical connection. The terms may refer to direct mutual connection, may also refer to indirect connection through a medium, or may refer to communication in two components or an interaction relationship of the two components. For those of ordinary skill in the art, specific meanings of the abovementioned terms in the present disclosure can be understood according to a specific condition.

In the present disclosure, unless otherwise explicitly specified and defined, a first feature "above" or "below" of a second feature may include that the first feature is in direct contact the second features, or may include that the first and second features are not in direct contact, but in contact through other features therebetween. In addition, the first feature "above", "over", and "on" the second feature, includes that the first feature is directly above and obliquely above the second feature, or only means that the horizontal height of the first feature is higher than that of the second feature. The first feature "under", "below", and "underneath" the second feature includes that the first feature is directly below and obliquely below the second feature, or only means that the horizontal height of the first feature is lower than that of the second feature.

In the present disclosure, terms "first", "second", "third", "fourth", etc. are merely used for description, and cannot be understood as indicating or implying relative importance. Terms "a plurality of" means two or more, unless otherwise limited explicitly and.

The above is only the preferred embodiments of the present invention, not intended to limit the present invention. As will occur to those skilled in the art, the present invention is susceptible to various modifications and changes. Any modifications, equivalent replacements, improvements and the like made within the spirit and principle of the present disclosure shall fall within the scope of protection of the present disclosure.

The invention claimed is:

1. A magnetic particle imaging method based on a non-ideal Field Free Point (FFP), comprising the following steps:
   S1, setting external magnetic field conditions of a non-ideal FFP and an ideal FFP, and obtaining a magnetization vector M of Superparamagnetic Iron Oxide Nanoparticles (SPIOs) and a Point Spread Function (PSF) in combination with a Langevin function;
   S2, obtaining a signal feature on basis of a voltage signal of a detection coil of a Magnetic Particle Imaging (MPI) instrument with the non-ideal FFP and the ideal FFP magnetic field conditions;
   S3, performing integral transformation on the voltage signal collected by the detection coil of the MPI instrument on basis of the signal feature obtained in S2, to obtain a voltage signal of an equivalent ideal FFP;
   S4, averaging a moving speed of an FFP of the MPI instrument on basis of the signal feature obtained in S2, to obtain a moving speed of the equivalent ideal FFP;
   S5, obtaining an equivalent Three-Dimensional (3D) concentration reconstruction image on basis of the voltage signal of the equivalent ideal FFP obtained in S3 and a moving speed of the equivalent ideal FFP obtained in S4.

2. The magnetic particle imaging method according to claim 1, wherein the external magnetic field conditions of the non-ideal FFP and the ideal FFP in S1 are as follows:
   a DC magnetic field intensity of all positions in the ideal FFP is G'=0, and an external AC driving magnetic field intensity $H_D$ is not affected:

$H_D = A \cos(2\pi f_D t)$;

wherein only a magnetic field intensity in a central area of the non-ideal FFP is H=0; wherein there is a static magnetic field with a DC magnetic field intensity of G in a peripheral area; wherein a magnetic field intensity on one side of the central area is G>0, and a magnetic field intensity on another side of the central area is G<0; wherein a combined excitation field produced by the static magnetic field and the external AC driving magnetic field is:

$H_{SPIO} = H_D + G = A \cos(2\pi f_D t) + G$ wherein, $H_D$ is the external AC driving magnetic field, A is an amplitude value of the AC driving magnetic field, $f_D$ is the frequency of the AC driving magnetic field, and t is time.

3. The magnetic particle imaging method according to claim 2, wherein the magnetization vector M is generated by the SPIOs according to Langevin function under action of the external magnetic field, to obtain the PSFs of the SPIOs at a non-ideal FFP and an ideal FFP:

$$PSF = \frac{dM}{dt}.$$

4. The magnetic particle imaging method according to claim 1, wherein S2 further comprising:
   a DC magnetic field intensity of each position at the ideal FFP is G'=0, and the voltage signal of the detection coil of the MPI instrument is the sum of PSFs at all positions S:

$$U_{ideal} = \sum_S PSF_{G'=0}$$

a DC magnetic field intensity of part positions $S_1$ of the non-ideal FFP is G>0, a DC magnetic field intensity of part positions $S_2$ is G=0, a DC magnetic field intensity of remaining positions $S_3$ is G<0, and the voltage signal of the detection coil is sum of the PSFs of three parts of positions:

$$U_{real} = \sum_{S_1} PSF_{G>0} + \sum_{S_2} PSF_{G=0} + \sum_{S_3} PSF_{G<0}$$

the voltage signal of the ideal FFP is compared with the voltage signal of the non-ideal FFP to obtain a common signal feature of the two.

5. The magnetic particle imaging method according to claim 4, wherein the common signal feature is in same half cycle, wherein integrals of voltage amplitudes along time are approximately equal:

$$\int_t U_{ideal} \approx \int_t U_{real}.$$

6. The magnetic particle imaging method according to claim 1, wherein S3 further comprising:
   performing integration on the voltage signal every half cycle along time to obtain a voltage signal of an equivalent ideal FFP, which is as follows:

$$\bar{u}(n) = \int_n^{n+\frac{T_0}{2}} u(t)dt$$

wherein, u(t) is voltage signal collected by the detection coil of the MPI instrument, $T_D$ is a cycle, $$\frac{1}{2}T_D = \frac{1}{2f_D},$$

and n=0, 1, 2 . . . .

7. The magnetic particle imaging method according to claim 1, wherein S4 further comprising:

averaging the moving speed of the FFP of instrument in every half cycle, to obtain moving speed of the equivalent ideal FFP:

$$\tilde{\dot{x}}_s(n) = \frac{\int_n^{n+\frac{T_D}{2}} \dot{x}_s(t)dt}{\frac{T_D}{2}}$$

wherein, $\dot{x}_s(t)$ is the moving speed of the FFP caused by a focusing field in the MPI instrument, and n=0, 1, 2 . . . .

8. The magnetic particle imaging method according to claim 1, wherein S5 further comprising:

dividing the voltage signal of equivalent ideal FFP by moving speed of the equivalent ideal FFP to obtain an image value at a corresponding position, which is as follows:

$$IMG_n = \tilde{u}(n)/\tilde{\dot{x}}_s(n);$$

splicing the image values at various positions according to a moving track of the FFP, to obtain an equivalent 3D concentration reconstruction image.

\* \* \* \* \*